(12) United States Patent
Cameretti et al.

(10) Patent No.: US 9,382,181 B2
(45) Date of Patent: *Jul. 5, 2016

(54) WORKUP OF A CYCLODODECANONE CYCLODODECANOL MIXTURE IN A SEQUENCE OF SIDE DRAW COLUMNS

(71) Applicant: Evonik Industries AG, Essen (DE)

(72) Inventors: Luca Cameretti, Dortmund (DE); Daniel Demicoli, Essen (DE); Ralf Meier, Dortmund (DE)

(73) Assignee: EVONIK DEGUSSA GmbH, Essen (DE)

( * ) Notice: Subject to any disclaimer, the term of this patent is extended or adjusted under 35 U.S.C. 154(b) by 105 days.

This patent is subject to a terminal disclaimer.

(21) Appl. No.: 14/105,587

(22) Filed: Dec. 13, 2013

(65) Prior Publication Data

US 2014/0171636 A1 Jun. 19, 2014

(30) Foreign Application Priority Data

Dec. 17, 2012 (DE) .......................... 10 2012 223 370

(51) Int. Cl.
| | | |
|---|---|---|
| *C07C 45/82* | (2006.01) | |
| *C07C 49/307* | (2006.01) | |
| *B01D 3/14* | (2006.01) | |
| *C07C 29/50* | (2006.01) | |
| *C07C 29/80* | (2006.01) | |
| *C07C 45/00* | (2006.01) | |
| *C07C 45/33* | (2006.01) | |

(52) U.S. Cl.
CPC ................ *C07C 45/82* (2013.01); *C07C 29/50* (2013.01); *C07C 29/80* (2013.01); *C07C 45/002* (2013.01); *C07C 45/33* (2013.01); *C07C 49/307* (2013.01); *B01D 3/143* (2013.01); *C07C 2101/20* (2013.01)

(58) Field of Classification Search
CPC .... B01D 3/143; C07C 49/307; C07C 49/413; C07C 29/80; C07C 29/50; C07C 45/002; C07C 48/82; C07C 45/82
See application file for complete search history.

(56) References Cited

U.S. PATENT DOCUMENTS

| | | | | |
|---|---|---|---|---|
| 2,337,489 | A * | 12/1943 | Patterson | .......................... 203/81 |
| 3,374,270 | A | 3/1968 | Hausen et al. | |
| 3,652,674 | A | 3/1972 | Hausen et al. | |
| 4,601,788 | A * | 7/1986 | Bannon | .......................... 202/153 |
| 5,200,040 | A * | 4/1993 | Naka et al. | ...................... 203/25 |
| 6,927,314 | B1 * | 8/2005 | Schultz et al. | ................ 585/734 |

(Continued)

FOREIGN PATENT DOCUMENTS

| | | |
|---|---|---|
| DE | 1568317 A1 | 7/1970 |
| DE | 2031782 A1 | 2/1971 |
| EP | 2336112 A1 | 6/2011 |
| GB | 930842 | 7/1963 |
| GB | 1 312 086 | 4/1973 |
| JP | 05-000977 A | 1/1993 |
| WO | WO2009092682 A2 | 7/2009 |

*Primary Examiner* — In Suk Bullock
*Assistant Examiner* — Jonathan Pilcher
(74) *Attorney, Agent, or Firm* — Oblon, McClelland, Maier & Neustadt, L.L.P.

(57) ABSTRACT

A process for removing a cyclododecanone-rich target fraction (A) from a dehydrogenation mixture (O) comprising low boilers (LB), cyclododecanone (CDON), medium boilers (MB), cyclododecanol (CDOL) and high boilers (HB) is provided. According to the process, substantially pure CDON is obtained via a distillative sequence of two side draw columns connected in series, wherein the sidestream of the primary side draw column is fed into the secondary side draw column. From the top of each of the two side draw columns, a CDON-rich fraction is drawn off, and these are combined to form a target fraction, which is essentially pure CDON.

13 Claims, 2 Drawing Sheets

(56) References Cited

U.S. PATENT DOCUMENTS

| | | | |
|---|---|---|---|
| 7,238,260 B2* | 7/2007 | Kahn et al. | 203/74 |
| 7,267,746 B1* | 9/2007 | Harris et al. | 202/160 |
| 7,351,311 B2* | 4/2008 | Windecker et al. | 203/75 |
| 7,431,805 B2* | 10/2008 | Beckman | 203/2 |
| 7,714,171 B2* | 5/2010 | Pinkos et al. | 568/365 |
| 2012/0103013 A1* | 5/2012 | King et al. | 62/625 |
| 2013/0118892 A1 | 5/2013 | Meier et al. | |

* cited by examiner

WORKUP OF A CYCLODODECANONE CYCLODODECANOL MIXTURE IN A SEQUENCE OF SIDE DRAW COLUMNS

CROSS REFERENCE TO RELATED APPLICATIONS

This application claims priority to German Application No. 102012223370.9, filed Dec. 17, 2012, the disclosure of which is incorporated herein by reference in its entirety.

BACKGROUND OF THE INVENTION

The invention relates to a process for removing a cyclododecanone-rich fraction from a dehydrogenation mixture comprising low boilers, cyclododecanone, medium boilers, cyclododecanol and high boilers. In the following description, terms and addreviations as defined in the following paragraphs will be employed.

Butadiene is used hereinafter as a short name for the substance 1,3-butadiene (CAS No. 106-99-0).

CDT is used hereinafter as an abbreviation for 1,5,9-cyclododecatriene (CAS No. 4904-61-4).

CDEN is used hereinafter as an abbreviation for cyclododecene (CAS No. 1501-82-2).

CDAN is used hereinafter as an abbreviation for cyclododecane (CAS No. 294-62-2).

CDON is used hereinafter as an abbreviation for cyclododecanone (CAS No. 830-13-7).

CDOL is used hereinafter as an abbreviation for cyclododecanol (CAS No. 1724-39-6).

CDOL t.q. stands for CDOL in technical-grade quality and refers to a mixture containing 75 to 85% by weight of CDOL and 10 to 20% by weight of CDON.

Oxime is used hereinafter as a short name for the oxime of CDON (CAS No. 9466-89-4).

Laurolactam is a common name for azacyclotridecan-2-one (CAS No. 947-04-6).

Laurolactam is the starting material of the production of the high-performance polymer nylon-12. Laurolactam may be obtained on the industrial scale via the following route: butadiene, which is obtained in mineral oil processing, may be converted by catalytic cyclotrimerization to CDT. Hydrogenation of CDT gives CDAN. Oxidation of CDAN with (atmospheric) oxygen results in a mixture of CDOL and CDON. This mixture is subjected to a dehydrogenation which converts the CDOL present in the mixture to CDON. A dehydrogenation mixture comprising principally CDON is obtained. In addition, the dehydrogenation mixture comprises unconverted CDOL and further components. High-purity CDON is separated from the dehydrogenation mixture. The high-purity CDON is oximated to its oxime. The oxime may subsequently be reacted with sulphuric acid to give laurolactam.

The overall process is described in greater detail in Oenbrink, G. and Schiffer, T. 2009. Cyclododecanol, Cyclododecanone, and Laurolactam. Ullmann's Encyclopedia of Industrial Chemistry. DOI: 10.1002/14356007.a08_201.pub2.

The present invention addresses the problem of workup of the CDON/CDOL-containing dehydrogenation mixture with the aim to obtain high-purity CDON.

The dehydrogenation mixture obtained by the route described above comprises, as well as CDON and CDOL, further components in the form of low boilers, medium boilers and high boilers.

"Low boilers" in the context of this invention are substances or substance mixtures which have a lower boiling point than CDON under the same pressure conditions and are therefore enriched in the distillate in the course of distillative separation of a mixture of low boilers and CDON. The significant low boilers in this connection include: cyclododecene (CDEN), cyclododecane (CDAN), dodecanal, and cyclododecane epoxide. Cyclododecane epoxide is at the limit of the above definition of the low boilers, since its boiling point of about 150° C. at 40 mbar corresponds virtually to that of CDON and it is therefore virtually inseparable in an economically viable manner from the CDON. Smaller amounts (less than 100 ppm) of the low boilers acetic acid and decane may also be present, but these are barely of any relevance for the separation tasks.

"Medium boilers" in the context of this invention are substances or substance mixtures which, under the same pressure conditions, have a higher boiling point than CDON and a lower boiling point than CDOL, and are therefore enriched in the middle of the column in the course of distillative separation of a mixture of CDON, medium boilers and CDOL. A medium boiler in this connection is particularly dodecan-1-ol. The fraction of the medium boilers may include further organic substances which have not been fully characterized to date.

"High boilers" in the context of this invention are substances or substance mixtures which, under the same pressure conditions, have a higher boiling point than CDOL and therefore remain in the residue in the distillative separation of a mixture of high boilers and CDOL. The high boiler limit is at about 180° C. and a pressure of 46 mbar. The high boilers include especially cyclododecanediol. In addition, the fraction of the high boilers comprises further organic substances which have not been characterized specifically to date.

The dehydrogenation of CDOL to CDON is described in DE1568317 and DE1248650. These describe dehydrogenation mixtures containing 74 to 89% by weight of CDON and 25.9 to 21.8% by weight of CDOL. The remaining fraction of the dehydrogenation mixture prepared is accounted for by low boilers and medium boilers. The workup of the dehydrogenation mixture is not described any further.

Japanese patent application JP05-000977A discloses a process for preparing high-purity CDOL from a CDON/CDOL mixture. During the distillative workup of the mixture, a small proportion of alkaline components is added to the mixture to be separated. A dividing wall column is not utilized for workup of the mixture.

The oxidation of CDAN to an oxidation mixture comprising CDAN and CDOL is described in GB930842. The processing steps according to the present invention are not disclosed.

DE2031782 describes a process for selective preparation of CDON, in which CDAN is oxidized in order to obtain a mixture of CDON and CDOL. The mixture is worked up by distillation, but without more specific description of the distillation operation.

WO2009/092682 discloses a process for workup of a CDON/CDOL-containing mixture, which is worked up with the aid of a dividing wall column. In this process, however, the medium boiler is the main component of the feed, while the low and high boilers are unwanted by-products.

The processing of a laurolactam-containing mixture in a dividing wall column is mentioned in EP2336112A1. According to the process described, the feed to the dividing wall column consists predominantly of medium boilers.

The CDON used for the preparation of laurolactam should be present in a form of maximum purity, since accompanying components cause lasting damage to the polymers in the nylon-12. These secondary components arise particularly during the oxidation of the CDAN and also during the dehydrogenation of the CDOL.

Thus there remains a need for a process for the workup of a mixture comprising low boilers, CDON, medium boilers, CDOL and high boilers which yields CDON of maximum purity.

SUMMARY OF THE INVENTION

This and other objectives have been achieved by the present invention, the first embodiment of which includes a process for removing a cyclododecanone-rich fraction (A) from a dehydrogenation mixture (O), the dehydrogenation mixture (O) comprising: low boilers (LB); cyclododecanone (CDON); medium boilers (MB); cyclododecanol (CDOL) and high boilers (HB); the process comprising:

a) feeding the dehydrogenation mixture (O) to a preliminary separator column;

b) distillatively removing the low boilers (LB) from the dehydrogenation mixture (O) to obtain a first mixture (ABC1) comprising cyclododecanone (CDON), medium boilers (MB), cyclododecanol (CDOL) and high boilers (HB);

c) feeding the first mixture (ABC1) into a primary side draw column (7);

d) drawing off a first cyclododecanone-rich fraction (A1) from the top of the primary side draw column (7);

e) drawing off a first fraction (C1) comprising cyclododecanol (CDOL) and high boilers (HB) from the bottom of the primary side draw column (7);

f) drawing off a second mixture (ABC2) comprising cyclododecanone (CDON), cyclododecanol (CDOL) and medium boilers (MB) from the side draw of the primary side draw column (7);

g) feeding the second mixture (ABC2) into a secondary side draw column (8);

h) drawing off a second cyclododecanone-rich fraction (A2) from the top of the secondary side draw column (8);

i) drawing off a second fraction (C2) comprising cyclododecanol (CDOL) and high boilers (HB) from the bottom of the secondary side draw column (8);

j) drawing off a third mixture (ABC3) comprising cyclododecanone (CDON), cyclododecanol (CDOL) and medium boilers (MB) from the side draw of the secondary side draw column (8);

k) combining the first cyclododecanone-rich fraction (A1) and the second cyclododecanone-rich fraction (A1) to obtain the cyclododecanone-rich target fraction (A).

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION OF THE PREFERRED EMBODIMENTS

Figure 1:
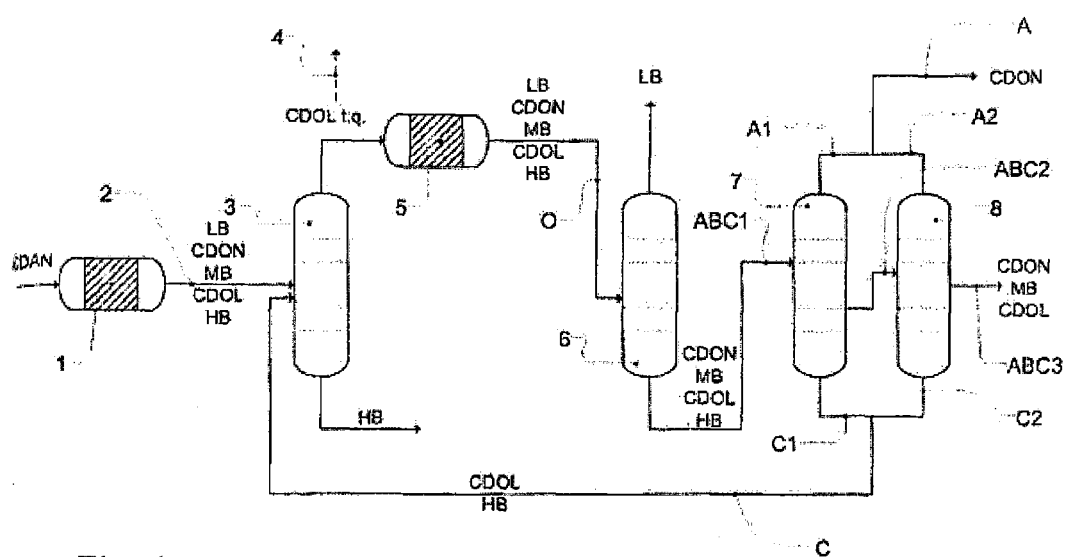
FIG. 1 shows a process flow diagram according to an embodiment of the present invention.

Throughout this description all ranges described include all values and sub-ranges therein, unless otherwise specified.

Additionally, the indefinite article "a" or "an" carries the meaning of "one or more" throughout the description, unless otherwise specified.

In a first embodiment, the present invention provides a process for removing a cyclododecanone-rich fraction (A) from a dehydrogenation mixture (O), the dehydrogenation mixture (O) comprising: low boilers (LB); cyclododecanone (CDON); medium boilers (MB); cyclododecanol (CDOL) and high boilers (HB); the process comprising:

a) feeding the dehydrogenation mixture (O) to a preliminary separator column;

b) distillatively removing the low boilers (LB) from the dehydrogenation mixture (O) to obtain a first mixture (ABC1) comprising cyclododecanone (CDON), medium boilers (MB), cyclododecanol (CDOL) and high boilers (HB);

c) feeding the first mixture (ABC1) into a primary side draw column (7);

d) drawing off a first cyclododecanone-rich fraction (A1) from the top of the primary side draw column (7);

e) drawing off a first fraction (C1) comprising cyclododecanol (CDOL) and high boilers (HB) from the bottom of the primary side draw column (7);

f) drawing off a second mixture (ABC2) comprising cyclododecanone (CDON), cyclododecanol (CDOL) and medium boilers (MB) from the side draw of the primary side draw column (7);

g) feeding the second mixture (ABC2) into a secondary side draw column (8);

h) drawing off a second cyclododecanone-rich fraction (A2) from the top of the secondary side draw column (8);

i) drawing off a second fraction (C2) comprising cyclododecanol (CDOL) and high boilers (HB) from the bottom of the secondary side draw column (8);

j) drawing off a third mixture (ABC3) comprising cyclododecanone (CDON), cyclododecanol (CDOL) and medium boilers (MB) from the side draw of the secondary side draw column (8);

k) combining the first cyclododecanone-rich fraction (A1) and the second cyclododecanone-rich fraction (A1) to obtain the cyclododecanone-rich target fraction (A).

The basic idea of the present invention is the use of a sequence of two series-connected side draw columns, wherein the sidestream of the primary side draw column is fed into the secondary side draw column. From the top of each of the two side draw columns, a CDON-rich fraction is drawn off, and these are combined to give a target fraction which is essentially pure CDON. The disruptive medium boilers are drawn off via the side. CDOL and the high boilers are separated off via the bottom.

In one preferred embodiment of the invention, the second mixture is drawn off in liquid form from the primary side draw column and introduced in liquid form into the secondary side draw column.

In order to ensure that exclusively liquid substances leave the side draw of the primary side draw column, the side draw should be disposed at a liquid collector in the primary side draw column. Liquid collectors are commonly known in distillation technology and serve primarily to collect the liquid flowing away from a bed of structured or random packing and to apply it to a liquid distributor which distributes the liquid homogeneously over a bed below. In the secondary side draw column, the second mixture is applied in liquid form like a feed. Therefore, preference may be given to exchanging an exclusively liquid stream between the two column sections.

In a very particularly preferred embodiment of the invention, the connection between the two side draw columns may be positioned such that the second mixture is drawn off at the separation plane in the primary side draw column at which the liquid concentration of the medium boilers in the primary side column is at a maximum, and that the second mixture is fed in at a separation plane in the secondary side draw column at which the composition of the second mixture corresponds essentially to the composition of the liquid phase at this separation plane in the secondary side draw column.

This means that, in the primary side draw column, the medium boilers are concentrated to a few percent and tapped off at the concentration peak, and this stream is fed back into the secondary column. The secondary column may then be operated with an elevated reflux ratio, such that the medium boilers can be concentrated to high values of up to 40% and withdrawn in the secondary sidestream.

The two bottom fractions comprising cyclododecanol and high boilers from the primary and secondary side draw columns may preferably be combined and fed to a distillation stage which at least partly removes the high boilers. This distillation stage may preferably be a preliminary separator column arranged between CDAN oxidation and CDOL dehydrogenation.

In one embodiment of the present invention, both side draw columns may be run under reduced pressure; i.e. at a pressure below 1 bar absolute. More particularly, the pressure in the two side draw columns should be below 50 mbar absolute.

One option is to generate the reduced pressure in the side draw columns with a common vacuum unit.

Preferably, the process according to the invention serves for workup of a dehydrogenation mixture having the following composition:

Low boilers (LB): 1 to 8% by weight, preferably 3% by weight;
Cyclododecanone (CDON): 60 to 90% by weight, preferably 70% by weight;
Medium boilers (MB): 0 to 1.5% by weight, preferably 1% by weight;
Cyclododecanol (CDOL): 10 to 40% by weight, preferably 24% by weight;
High boilers (HB): 0.1 to 2.5% by weight, preferably 2% by weight;
wherein the sum of the weight percentages is 100%.

The process preferably serves to obtain a target fraction having a particularly high purity. According to the invention, the target fraction should have a CDON content of at least 98%, preferably even a target CDON content of 99.5% by weight. In addition, the cyclododecanone-rich fractions drawn off at the top of the side draw columns should as far as possible be free of CDOL, high boilers and medium boilers. The fractions drawn off at the bottom of the side draw columns should accordingly be substantially free of CDON.

If the process according to the invention is used in the course of a laurolactam process, the dehydrogenation mixture may be obtained by a process comprising:

l) oxidation of cyclododecane with oxygen to obtain an oxidation mixture comprising low boilers, cyclododecanone, medium boilers, cyclododecanol and high boilers;

m) distillatively removing a cyclododecanol-rich fraction from the oxidation mixture, said fraction having been depleted of high boilers;

n) dehydrogenating the cyclododecanol-rich fraction to obtain the dehydrogenation mixture.

If the process according to the invention is part of a laurolactam process, it may be advisable to recycle the bottoms from the two side draw columns into m) conducted in the preliminary separator column. This is because the bottom fractions comprise a large portion of CDOL, which can be made available again to the dehydrogenation operation and converted to CDON in this way. The high boilers may be concentrated up to a limiting concentration and are circulated therewith. The high boilers newly introduced into the process via the oxidation leave the process again via the bottom of the preliminary separator column and via the secondary side draw.

The combined top product of the side draw columns is high-purity CDON, which is of excellent suitability to be oximated and then processed further to give laurolactam. The mixture provided via the secondary side draw can be utilized either physically or thermally. It may preferably be utilized physically, by collecting the mixture and separating it by a batch distillation. The goal of this distillation is to obtain the remaining fractions of CDON. However, if this means an unacceptable level of cost and inconvenience, the third mixture provided via the secondary side draw may be incinerated. The tangible heat can optionally be tapped off beforehand.

Having generally described this invention, a further understanding can be obtained by reference to certain specific examples which are provided herein for purposes of illustration only and are not intended to be limiting unless otherwise specified.

The overall workup operation is shown in FIG. 1. It commences in an oxidation 1 in which CDAN is oxidized with oxygen. This gives an oxidation mixture 2 comprising low boilers LB, CDON, medium boilers MB, CDOL and high boilers HB. On the basis of the reaction mechanism, the CDON content within the oxidation mixture 2 is much lower than the CDOL content. Typically, such an oxidation mixture 2 contains about 15% by weight of CDON and about 70% by weight of CDOL.

The oxidation mixture 2 is fed into a preliminary separator column 3. The function of this preliminary separator column 3 is to discharge a large proportion of the high boilers HB. This is done via the bottom. CDOL t.q. is drawn off via the top of the preliminary separator column 3. CDOL t.q. contains about 84% by weight of CDOL and 13% by weight of CDON. CDOL t.q. constitutes a separate saleable product and can optionally be discharged from the process via a branch 4.

For the laurolactam preparation, CDOL t.q. is subjected to a dehydrogenation 5. This dehydrogenates CDOL to CDON, such that the proportion of these two substances is reversed. The dehydrogenation mixture O drawn off from the dehydrogenation 5 typically has the following composition:

Low boilers (LB): 1 to 8% by weight, preferably 3% by weight;
Cyclododecanone (CDON): 60 to 90% by weight, preferably 70% by weight;
Medium boilers (MB): 0 to 1.5% by weight, preferably 1% by weight;
Cyclododecanol (CDOL): 10 to 40% by weight, preferably 24% by weight;
High boilers (HB): 0.1 to 2.5% by weight, preferably 2% by weight;
wherein the sum of the weight percentages is 100%.

The dehydrogenation mixture O is then fed into a low boiler column 6. The purpose of the low boiler column 6 is to remove the low boilers LB by overhead distillation out of the dehydrogenation mixture O, such that a first mixture ABC1 comprising CDON, medium boilers MB, CDOL and high boilers HB is obtained at the bottom of the low boiler column 6. The low boilers LB are preferably removed completely in this step. The special feature of the bottom product ABC1 is that its content of medium boilers MB is extremely low, namely only about 1% by weight. For the rest, the mixture ABC1 consists essentially of CDON, CDOL and high boilers HB. A typical composition of the mixture ABC1, is:

Low boilers (LB): 0 to 1% by weight, preferably 0% by weight;
Cyclododecanone (CDON): 60 to 90% by weight, preferably 70% by weight;
Medium boilers (MB): 0 to 2% by weight, preferably 1% by weight;
Cyclododecanol (CDOL): 10 to 40% by weight, preferably 26% by weight;
High boilers (HB): 0.1 to 3% by weight, preferably 3% by weight;
wherein the sum of the weight percentages is 100%.

Mixture ABC1 is then fed into a primary side draw column 7. From the top of the primary side draw column 7, a CDON-rich fraction A1 is drawn off. Preferably, the proportion of CDON in fraction A1 is at least 95% by weight. Ideally, the top product A1 is free of CDOL, medium boilers MB and high boilers HB, which cannot be achieved in practice with an economically acceptable level of cost and inconvenience. However, a purity of >99% by weight may be achieved.

A typical composition of the mixture A1, may be:
Low boilers (LB): 0 to 1% by weight, preferably 0% by weight;
Cyclododecanone (CDON): 95 to 100% by weight, preferably 99.5% by weight;
Medium boilers (MB): 0 to 1% by weight, preferably 0.25% by weight;
Cyclododecanol (CDOL): 0 to 1% by weight, preferably 0.25% by weight;
High boilers (HB): 0 to 0.5% by weight, preferably 0% by weight;
wherein the sum of the weight percentages is 100%.

At the bottom of the primary side draw column 7, a first fraction C1 comprising CDOL and high boilers HB is drawn off. Ideally, this is free of medium boilers MB and CDON.

A typical composition of the mixture C1, may be:
Low boilers (LB): 0 to 1% by weight, preferably 0% by weight;
Cyclododecanone (CDON): 0 to 1% by weight, preferably 0% by weight;
Medium boilers (MB): 0 to 1% by weight, preferably 0.2% by weight;
Cyclododecanol (CDOL): 85 to 95% by weight, preferably 90% by weight;
High boilers (HB): 5 to 15% by weight, preferably 9.8% by weight;
wherein the sum of the weight percentages is 100%.

From the side draw of the primary side draw column 7, a second mixture ABC2 is drawn off. ABC2 may have the following composition:
Cyclododecanone (CDON): 30 to 50% by weight, preferably 43% by weight;
Medium boilers (MB): 0 to 20% by weight, preferably 18% by weight;
Cyclododecanol (CDOL): 30 to 50% by weight, preferably 38.4% by weight;
High boilers (HB): 0.1 to 2% by weight, preferably 0.6% by weight;
wherein the sum of the weight percentages is 100%.

Mixture ABC2 is drawn off in liquid form from the primary side draw column 7. For this purpose, the side draw is disposed at a liquid collector (not shown). The side draw is at the separation plane at which the concentration of the medium boilers in the primary side draw column 7 is at a maximum. Details in this regard are elucidated with reference to FIG. 2.

The second mixture ABC2 is fed into a secondary side draw column 8 in liquid form. This is done at the separation plane at which the composition of the liquid phase within the secondary side draw column 8 corresponds essentially to that of the mixture ABC2. Details in this regard are elucidated with reference to FIG. 2.

From the top of the secondary side draw column 8, a second CDON-rich fraction A2 is drawn off. Preferably, the proportion of CDON in fraction A2 is at least 97% by weight. Ideally, the top product A2 may be free of CDOL, medium boilers MB and high boilers HB, which cannot be achieved in practice with an economically acceptable level of cost and inconvenience. However, a purity of >99% by weight can be achieved.

A typical composition of the mixture A2, may be:
Low boilers (LB): 0 to 1% by weight, preferably 0% by weight;
Cyclododecanone (CDON): 97 to 100% by weight, preferably 99.9% by weight;
Medium boilers (MB): 0 to 1% by weight, preferably 0.05% by weight;
Cyclododecanol (CDOL): 0 to 1% by weight, preferably 0.05% by weight;
High boilers (HB): 0 to 0.5% by weight, preferably 0% by weight;
wherein the sum of the weight percentages is 100%.

At the bottom of the secondary side draw column 8, a second fraction C2 comprising CDOL and high boilers HB is drawn off. Ideally, this may be free of medium boilers MB and CDON.

A typical composition of the mixture C2, may be:
Low boilers (LB): 0 to 1% by weight, preferably 0% by weight;
Cyclododecanone (CDON): 0 to 1% by weight, preferably 0% by weight;
Medium boilers (MB): 0 to 1% by weight, preferably 0.2% by weight;
Cyclododecanol (CDOL): 85 to 95% by weight, preferably 90% by weight;
High boilers (HB): 5 to 15% by weight, preferably 9.8% by weight; wherein the sum of the weight percentages is 100%.

Via the side draw of the secondary side draw column 8, a third mixture ABC3 rich in medium boilers is drawn off. It comprises essentially CDON, CDOL and medium boilers. The medium boilers MB constitute the greatest proportion of the side mixture ABC3. The proportion of the products of value CDON and CDOL is relatively low. The stream ABC3 withdrawn via the side draw of the secondary side draw column 8 typically has the following composition:
Cyclododecanone (CDON): 20 to 50% by weight, preferably 35% by weight;
Medium boilers (MB): 0 to 60% by weight, preferably 30% by weight;
Cyclododecanol (CDOL): 10 to 50% by weight, preferably 30% by weight;
High boilers (HB): 0 to 2% by weight, preferably 1% by weight; wherein the sum of the weight percentages is 100%.

The mixture ABC3 drawn off via the side draw of the secondary side draw column 8 may be utilized either physically or thermally. Preference may be given to a physical utilization which involves collecting ABC3 and subjecting it to a batch distillation. In this way, the valuable CDON can be obtained from ABC3. Alternatively, ABC3 can be incinerated. If possible, the tangible heat carried by ABC3 should be tapped off beforehand.

The two top products A1 and A2 are combined to give a fraction A, which may be virtually pure CDON. This high-purity CDON mixture suitable for laurolactam preparation constitutes the target fraction of the process. Target fraction A consists to an extent of at least 98% by weight of CDON, preferably even to an extent of 99.5% by weight of CDON.

The two bottom products C1 and C2 are combined to give a fraction C which comprises essentially CDOL and high boilers HB. The combined bottoms fraction C is recycled and conducted together with the oxidation mixture 2 into the preliminary separator column 3. In this way, the unconverted CDOL is sent back to the dehydrogenation 5. The high boilers HB returned are concentrated in the process to a certain degree. The high boilers HB freshly introduced from the oxidation 1 are separated out via the bottoms from the preliminary separator column 3, such that a steady state is established with regard to the high boiler concentration.

Figure 2:
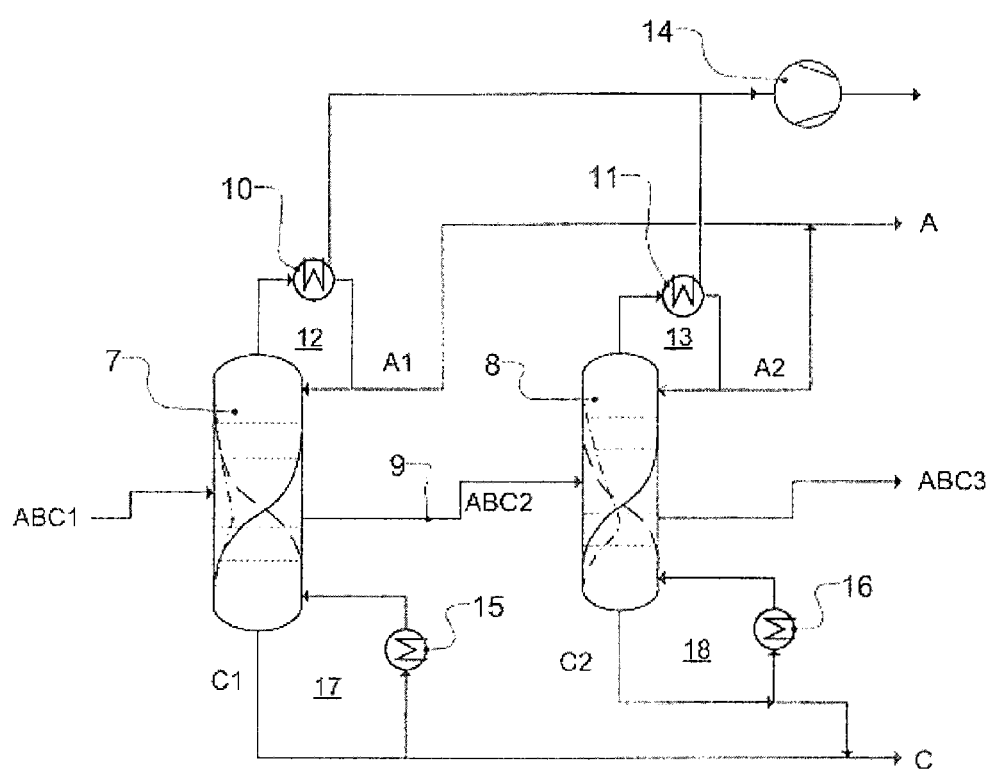
FIG. 2 shows the process flow detail of one preferred embodiment of the present invention.

The schematic setup of the two series-connected side draw columns 7, 8 is shown in more detail in FIG. 2.

It should first be mentioned that, a multitude of internals known per se may be installed in the two columns 7, 8, for example structured packings or random packings from Sulzer or Montz. The purpose of the internals is to achieve a maximum number of theoretical plates. Preferably, the two columns 7, 8 may have the following number of theoretical plates:

Primary side draw column 7: 75 theoretical plates

Secondary side draw column 8: 75 theoretical plates

In addition, various conventionally known liquid collectors and distributors may be provided in the two columns 7, 8.

In one embodiment of the present invention, an essential element of the inventive sequence of the two side draw columns 7, 8 is the connection 9 which connects the side draw of the primary side draw column 7 to the inlet of the secondary side draw column 8. The connection 9 is a liquid conduit provided with a circulation pump, which is not shown, to establish a flow through the conduit. By the connection 9, liquid medium boiler may be transferred from the concentration maximum thereof in the primary side draw column 7 to the secondary side draw column 8. In order to ensure that exclusively liquid substances are exchanged via the connection 9, the connection 9 originates from a liquid collector in the primary side draw column 7. The liquid collector may be installed at a separation plane at which the liquid concentration of the medium boilers has a maximum. The connection 9 thus originates at the separation plane of the primary side draw column 7 at which the liquid concentration in the medium boiler in this column 7 is at a maximum. The connection 9 opens out at the separation plane of the secondary side draw column 8 at which the composition of the liquid phase corresponds as far as possible to that of the liquid mixture ABC2 withdrawn from the primary side draw column 7. This means that the medium boiler is concentrated to a few per cent in the primary side draw column 7 and tapped off at the concentration peak, and this stream ABC2 is introduced via the connection 9 to the secondary side draw column 8. The draw and feed points for the connection 9 are accordingly selected in accordance with the concentration ratios and need not be on the same plane.

In terms of the abovementioned number of theoretical plates, the feed and draw points for mixtures ABC1, ABC2 and ABC3 may preferably be disposed at the following plates in the appropriate column (counted from the top):

|  | ABC 1 | ABC 2 | ABC 3 |
|---|---|---|---|
| Feed: | 35 | 60 | — |
| Draw: | — | 65 | 55 |

From the tops of each of the two side draw columns 7, 8, a gaseous top product A1, A2 is drawn off, comprising almost exclusively CDON. As usual in distillation columns, a condenser 10, 11 and a tops return 12, 13 are provided in each case at the top draw. A common vacuum system 14 generates a reduced pressure of about 40 mbar absolute in the two side draw columns 7, 8.

The return ratio v may be selected under the conditions outlined as follows:

Primary side draw column 7: v=4.3

Secondary side draw column 8: v=3.5

At the bottoms of each of the two side draw columns 7, 8, a liquid fraction C1, C2 is drawn off, comprising predominantly CDOL and high boilers. As usual in distillation columns, a reboiler/vaporizer 15, 16 with a corresponding bottoms return 17, 18 may be provided here.

FIG. 2 also shows the concentration profiles of CDON (solid line, fraction A), CDOL (broken line, fraction C) and medium boilers (line of dashes and dots, fraction B). The connection 9 is arranged such that it originates at the separation plane of the primary column 7 at which the liquid concentration in the medium boiler is at a maximum. The connection opens out at the separation plane of the secondary side draw column 8 at which the composition of the liquid phase corresponds as far as possible to that of the liquid stream ABC2 withdrawn from the primary column. This means that the medium boiler is concentrated to a few percent in the primary column and tapped off at the concentration peak, and this stream is fed back via the connection 9 into the secondary column. In this way, the mixture ABC1 is separated in the primary column such that CDON is obtained as a pure distillate and CDOL as a pure high boiler. The medium boiler forms a concentration peak within the primary column. At the point of the concentration maximum, a substream of liquid medium boiler is withdrawn and transferred via the connection 9 into the secondary column. A sharp separation of CDON and CDOL is again conducted there with elevated reflux. The medium boiler is in turn highly concentrated within the secondary column and can be removed via the sidestream ABC3.

Numerous modifications and variations on the present invention are possible in light of the above description. It is therefore to be understood that within the scope of the following Claims, the invention may be practiced otherwise than as specifically described herein. Any such embodiments are intended to be within the scope of the present invention.

LIST OF REFERENCE NUMERALS

1 Oxidation
2 Oxidation mixture
3 Preliminary separator column
4 Branch
5 Dehydrogenation
6 Low boiler column
7 Primary side draw column
8 Secondary side draw column
9 Connection
10 Condenser of the primary side draw column
11 Condenser of the secondary side draw column
12 Tops return of the primary side draw column 13 Tops return of the secondary side draw column
14 Vacuum system
15 Reboiler/vaporizer of the primary side draw column
16 Reboiler/vaporizer of the secondary side draw column
17 Bottoms return of the primary side draw column
18 Bottoms return of the secondary side draw column
O Dehydrogenation mixture
A Target fraction
A1 Top product of the primary side draw column
A2 Top product of the secondary side draw column
C CDON/high boiler-containing fraction
C1 Bottom product of the primary side draw column
C2 Bottom product of the secondary side draw column
ABC1 First mixture (feed of primary side draw column)
ABC2 Second mixture (primary side draw)
ABC3 Third mixture (secondary side draw)

The invention claimed is:

1. A process for removing a cyclododecanone-rich fraction (A) from a dehydrogenation mixture (O), the dehydrogenation mixture (O) comprising: components having a boiling point less than cyclododecanone (CDON) (LB); cyclododecanone (CDON);
   components having a boiling point between CDON and cyclododecanol (CDOL) (MB);
   cyclododecanol (CDOL); and
   components having a boiling point above CDOL (HB);
   the process comprising:
   a) feeding the dehydrogenation mixture (O) to a preliminary separator column;
   b) distillatively removing the LB components from the dehydrogenation mixture (O) to obtain a first mixture (ABC1) comprising the cyclododecanone (CDON), the MB components, the cyclododecanol (CDOL) and the HB components;
   c) feeding the first mixture (ABC1) into a primary side draw column (7);
   d) drawing off a first cyclododecanone-rich fraction (A1) from the top of the primary side draw column (7);
   e) drawing off a first fraction (C1) comprising cyclododecanol (CDOL) and the HB components from the bottom of the primary side draw column (7);
   f) drawing off a second mixture (ABC2) comprising cyclododecanone (CDON), cyclododecanol (CDOL) and the MB components from the side draw of the primary side draw column (7);
   g) feeding the second mixture (ABC2) into a secondary side draw column (8);
   h) drawing off a second cyclododecanone-rich fraction (A2) from the top of the secondary side draw column (8);
   i) drawing off a second fraction (C2) comprising cyclododecanol (CDOL) and the HB components from the bottom of the secondary side draw column (8);
   j) drawing off a third mixture (ABC3) comprising cyclododecanone (CDON), cyclododecanol (CDOL) and the MB components from the side draw of the secondary side draw column (8);
   k) combining the first cyclododecanone-rich fraction (A1) and the second cyclododecanone-rich fraction (A1) to obtain the cyclododecanone-rich target fraction (A).

2. The process according to claim 1, wherein the second mixture (ABC2) is drawn off in liquid form from the primary side draw column and introduced in liquid form into the secondary side draw column.

3. The process according to claim 2, wherein the second mixture (ABC2) is drawn off at a separation plane of the primary side draw column at which the liquid concentration of the MB components in the primary side column is at a maximum, and in that the second mixture (ABC2) is fed in at a separation plane of the secondary side draw column at which the MB component composition corresponds essentially to the composition of the liquid phase at the feed separation plane of the primary side draw column.

4. The process according to claim 1, further comprising feeding the first fraction (C1) comprising cyclododecanol (CDOL) and the HB components and the second fraction (C2) comprising cyclododecanol (CDOL) and the HB components in combination to a distillation stage which at least partly removes the high boilers.

5. The process according to claim 1, wherein both side draw columns are operated at a pressure below 1 bar absolute.

6. The process according to claim 5, wherein the reduced pressure in the side draw columns is generated by a common vacuum unit.

7. The process according to claim 1, wherein a composition of the dehydrogenation mixture (O) is:
   Low boilers (LB): 1 to 8% by weight;
   Cyclododecanone (CDON): 60 to 90% by weight;
   Medium boilers (MB): 0 to 1.5% by weight;
   Cyclododecanol (CDOL): 10 to 40% by weight;
   High boilers (HB): 0.1 to 2.5% by weight;
   wherein a sum of the weight % values is 100%.

8. The process according to claim 1, wherein a content of cyclododecanone (CDON) in the cyclododecanone-rich target fraction (A) is at least 98% by weight.

9. The process according to claim 1, wherein the cyclododecanone-rich target fraction (A) is free of cyclododecanol (CDOL), high boilers (HB) and medium boilers (MB).

10. The process according to claim 1, wherein each of the fractions (C1, C2) comprising cyclododecanol (CDOL) and the HB components is free of cyclododecanone (CDON).

11. The process according to claim 1, wherein the dehydrogenation mixture (O) is obtained by a process comprising:
   l) oxidation of cyclododecane (CDAN) with oxygen to obtain an oxidation mixture (2) comprising the LB components, cyclododecanone (CDON), the MB components, cyclododecanol (CDOL) and the HB components
   m) distillatively removing a cyclododecanol-rich fraction (CBOL technical quality) (CDOL t.q.) from the oxidation mixture (2);
   n) removing the high boilers from the CDOL t.q. to obtain a fraction (C) comprising cyclododecanol (CDOL) and high boilers (HB); and
   o) dehydrogenating the cyclododecanol-rich fraction from which the high boilers are removed to obtain the dehydrogenation mixture (O).

12. The process according to claim 11, wherein the fractions (C1, C2) comprising cyclododecanol (CDOL) and high boilers (HB) are recycled into distillation m).

13. The process according to claim 1, further comprising:
   oximating the cyclododecanone-rich fraction (A) to obtain an oxime of cyclododecanone; and
   reacting the cyclododecane oxime with sulfuric acid to obtain laurolactam.

* * * * *